(12) United States Patent
Seul et al.

(10) Patent No.: US 9,670,534 B2
(45) Date of Patent: Jun. 6, 2017

(54) METHODS FOR ARRAY ASSEMBLY AND DETECTION INVOLVING ELONGATION OF SELF-COMPLEMENTARY LOOPED PROBES

(71) Applicant: BioArray Solutions, Ltd., Warren, NJ (US)

(72) Inventors: Michael Seul, Fanwood, NJ (US); Yi Zhang, Hillsborough, NJ (US); Sukanta Banerjee, Pennington, NJ (US); Jiacheng Yang, Hillsborough, NJ (US); Chiu Chau, Edison, NJ (US)

(73) Assignee: BioArray Solutions, Ltd., Warren, NJ (US)

( * ) Notice: Subject to any disclaimer, the term of this patent is extended or adjusted under 35 U.S.C. 154(b) by 283 days.

(21) Appl. No.: 14/449,569

(22) Filed: Aug. 1, 2014

(65) Prior Publication Data

US 2015/0126389 A1 May 7, 2015

Related U.S. Application Data

(63) Continuation of application No. 12/708,362, filed on Feb. 18, 2010, now Pat. No. 8,795,966, which is a continuation of application No. 11/403,100, filed on Apr. 12, 2006, now abandoned.

(51) Int. Cl.
*C12Q 1/68* (2006.01)

(52) U.S. Cl.
CPC ......... *C12Q 1/6837* (2013.01); *C12Q 1/6818* (2013.01); *C12Q 1/6827* (2013.01)

(58) Field of Classification Search
None
See application file for complete search history.

(56) References Cited

U.S. PATENT DOCUMENTS

| | | | |
|---|---|---|---|
| 2002/0130363 A1* | 9/2002 | Yamazaki | G02F 1/136213 257/353 |
| 2003/0180508 A1* | 9/2003 | McArdle | G03F 7/34 428/195.1 |
| 2005/0170089 A1* | 8/2005 | Lashmore | B82Y 10/00 427/248.1 |

OTHER PUBLICATIONS

Yellin et al. Printing superparamagnetic colloidal particle arrays on patterned magnetic film. Journal of Applied Physics 93(10): 7331-7333; May 15, 2003.*

(Continued)

*Primary Examiner* — Samuel Woolwine
(74) *Attorney, Agent, or Firm* — Mintz, Levin, Cohn, Ferris, Glovsky and Popeo P.C.

(57) ABSTRACT

Disclosed herein are methods for array assembly and detection. The methods can use an incubation chamber containing a suspension of nucleic acid targets, polymerase and a set of oligonucleotide probes bound to magnetic beads in a randomly dispersed state. Each probe can have a target binding domain that is complementary to a target nucleic acid, a closing domain with a sequence that is complementary to the sequence of the target binding domain, and a joining region between the binding domain and the closing domain, which is not complementary to the target nucleic acid. Method steps can include providing the incubation chamber, placing the incubation chamber in a magnetic trap, generating a magnetic field that induces the magnetic beads to migrate towards a substrate and, once in proximity to the substrate, to interact with each other repulsively and reorganize into arrays, and imaging the array.

18 Claims, 17 Drawing Sheets

(56) References Cited

OTHER PUBLICATIONS

Doyle et al. Self-assembled magnetic matrices for DNA separation chips. Science 295:2237; Mar. 2002.*
Yamamuro et al. Structure of self-assembled Fe and FePt nanoparticle arrays. Mat. Res. Soc. Symp. 636:D10 8.1-8.6; 2001.*
Yellin et al. Programmable assembly of colloidal particles using magnetic microwell templates. Langmuir 20:2553-2559; 2004.*

* cited by examiner

METHODS FOR ARRAY ASSEMBLY AND DETECTION INVOLVING ELONGATION OF SELF-COMPLEMENTARY LOOPED PROBES

BACKGROUND

Molecular Stringency in Multiplexed Assays—

A self-complementary oligonucleotide capture probe in a "looped" configuration may be used to adjust molecular stringency in an assay. Assay stringency relates to the positive results produced by an assay, such that high stringency conditions generate relatively fewer positive results than lower stringency conditions. Looped probes are described in WO 01/98765, entitled: "Multianalyte Molecular Analysis Using Application-Specific Random Particle Arrays" and U.S. Pat. No. 6,361,945 (assigned to Gen Probe, Inc.). Such a probe consists of a 5'-terminal subsequence and a complementary 3'-terminal subsequence, tethered by an unrelated subsequence, the two terminal subsequences capable of forming a duplex ("stem"), and the tether forming a loop, and either the 5'-terminal subsequence of the 3'-terminal subsequence capable of forming a duplex with a target nucleic acid. The probe may be attached to a solid phase such as an encoded microparticle ("bead"), by way of an appropriate functional modification of the 5'terminal subsequence or the loop subsequence.

Using a fluorescence acceptor and a proximal fluorescence quencher (as discussed in U.S. Pat. No. 6,534,274), capture of a target nucleic acid is detected by way of detecting a transition from the Closed ("C") state of the capture probe to the Open ("O") state or the target-associated ("OT") state, the O-state contributing to "background" fluorescence, independent of target concentration (FIG. 1). In this competitive equilibrium, low stringency, favoring the closed state, will reduce the likelihood of formation of the open (or other intermediate state, see Detailed Description, below) required for probe-target duplex formation, thereby diminishing the detection sensitivity. Conversely, high stringency, favoring the open state, will likewise reduce the likelihood of target capture—by reducing the stability of any probe-target duplex—while producing indiscriminate fluorescence, independent of captured target, thereby reducing specificity.

Thus, the use of a looped probe calls for resolution of the conflict between detection sensitivity and specificity, preferably by operating near an optimal stringency, determined by a choice of buffer conditions and operating temperature. For typical buffer conditions, which generally are of low ionic strength, e.g. corresponding to salt concentrations of 50 mM, this step requires selection of an optimal detection temperature, preferably at or above the range of the midpoint of the melting curve where specificity is optimal. Optimal stringencies generally will depend on capture probe sequences, and on target configuration and/or length. Thus, identifying the optimal stringency range in a multiplexed assay thus becomes increasingly difficult with each different probe added, given the dispersion of the melting curve profiles of a set of different probe-target complexes under given assay conditions.

SUMMARY OF THE INVENTION

Disclosed are methods of enhancing detection sensitivity and expanding the range of stringencies compatible with detection of specific targets, especially where there is a low target concentration, as typically encountered in, e.g., the detection of genomic material from infectious agents (see e.g., Chen, Martinez & Mulchandani, "Molecular Beacons: A Real-Time Polymerase Chain Reaction Assay for Detecting *Salmonella*," Analytical Biochemistry 280, 166-172 (2000)). Also disclosed is a method of enhancing detection sensitivity by providing for target capture to a self complementary ("looped") probe, anchored, preferably by its loop subsequence, at a lateral density of at least a certain preset minimum, on a solid phase carrier, preferably a microparticle ("bead").

Further disclosed is a method of stabilizing a probe-target complex under conditions of high stringency by providing for target-mediated, enzyme-catalyzed elongation of the 3'-terminal probe subsequence to convert the probe-target complex ("OT"), formed as a result of target capture and characterized by fluorescence, into an elongation product ("eOT") of enhanced thermodynamic stability (FIG. 2). The formation of the eOT state can be detected by temperature cycling: the eOT complex may be exposed to higher temperatures without loss of fluorescence—which would otherwise result, for a non-elongated complex (in the OT state), from the release of the target at the higher temperature and formation of the closed ("C") state of the probe—upon subsequent return to lower temperature.

The formation of this elongation product has at least a three-fold benefit:

(i) enhance the sensitivity of target detection—by converting the C state of the probe into the eOT state; even under conditions of extreme stringency, selected, for example, to ensure enzymatic efficiency particularly in homogeneous assay designs ((see e.g. "Transcription Amplification System with Integrated Multiplex Detection; Functional Integration of Capture, Amplification and Multiplex Detection" filed Sep. 2, 2005; Ser. No. 11/218,838, incorporated by reference), this conversion ensures high detection sensitivity by accumulation of elongation product, over an extended period of time, by way of random fluctuations of the closed into the open (or related reactive intermediate, see below) state permitting target capture and enzyme-catalyzed elongation; to the extent that the eOT state is irreversible under prevailing assay conditions, this conversion is akin to a digital "ON" signal;

(ii) enhance the range of optimal stringency of a multiplexed assay—essentially by raising melting temperatures and thereby avoiding operation in the range of temperatures coinciding with dispersion in the melting curves of multiple distinct probe-target pairs; and (iii) enable the application of allele-specific detection and implementation of a phasing strategy, in analogy to the phasing method described in U.S. patent application Ser. No. 10/271,602, entitled: "Multiplexed Analysis of Polymorphic Loci by Concurrent Interrogation and Enzyme-Mediated Detection," incorporated by reference.

DETAILED DESCRIPTION

Figure 1:
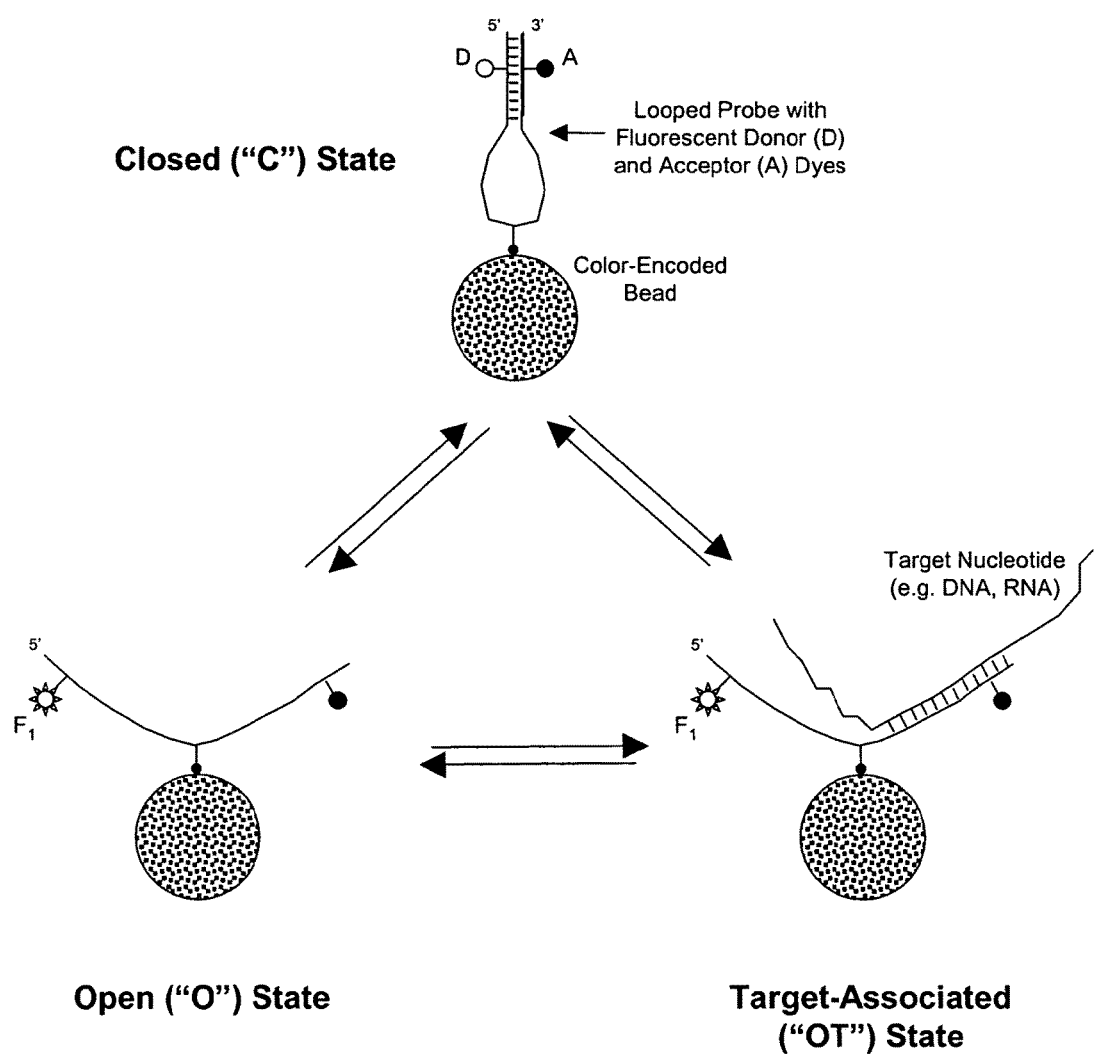
FIG. 1 is an illustration showing the closed ("C"), open ("O"), and target-associated ("OT") states of a self-complementary ("looped") capture probe.
Figure 2A:
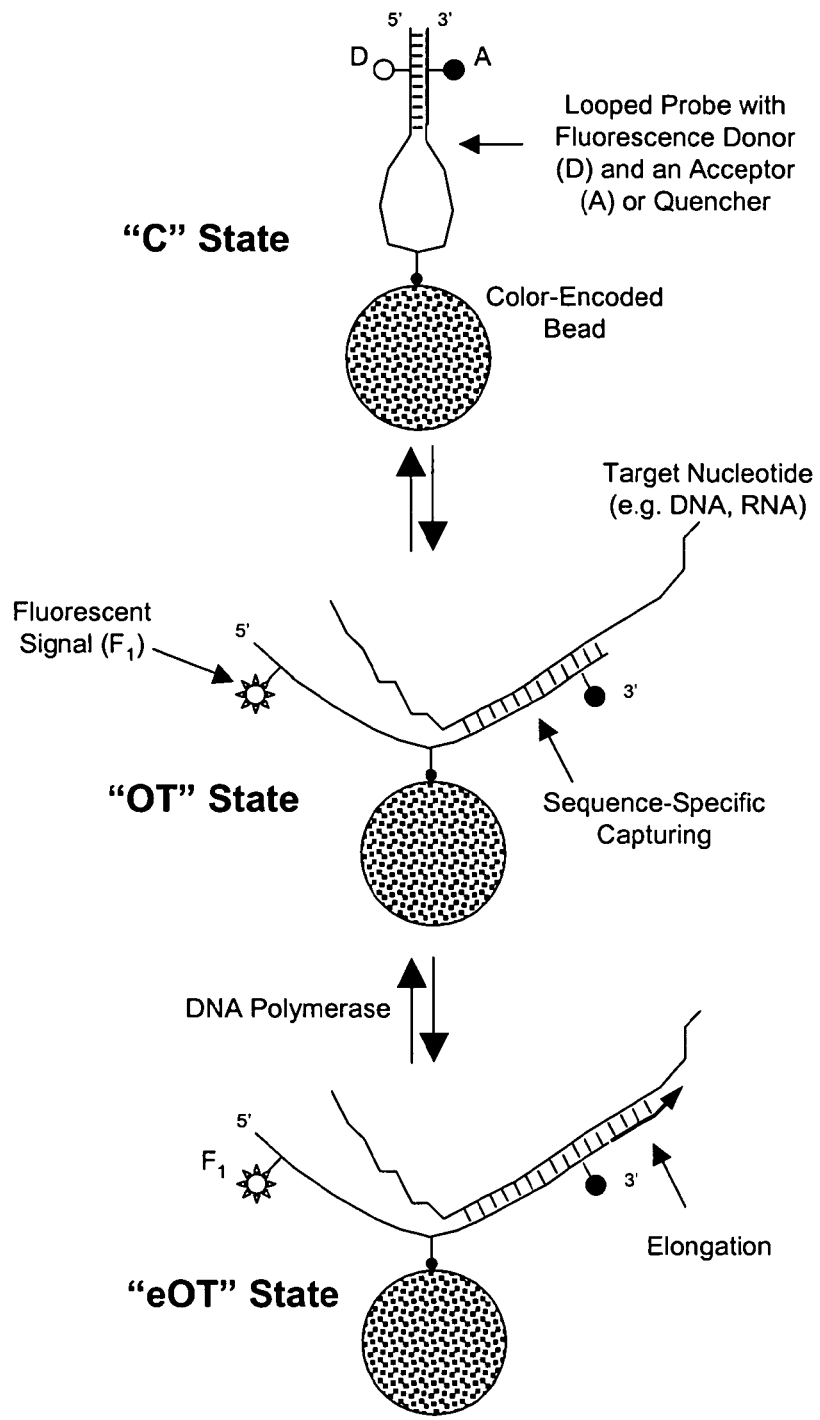
FIG. 2A is an illustration showing the target-mediated, enzymatic elongation of a looped probe labeled with a fluorescence donor on the 5'-terminal subsequence and an acceptor on the 3'-terminal subsequence.
Figure 2B:
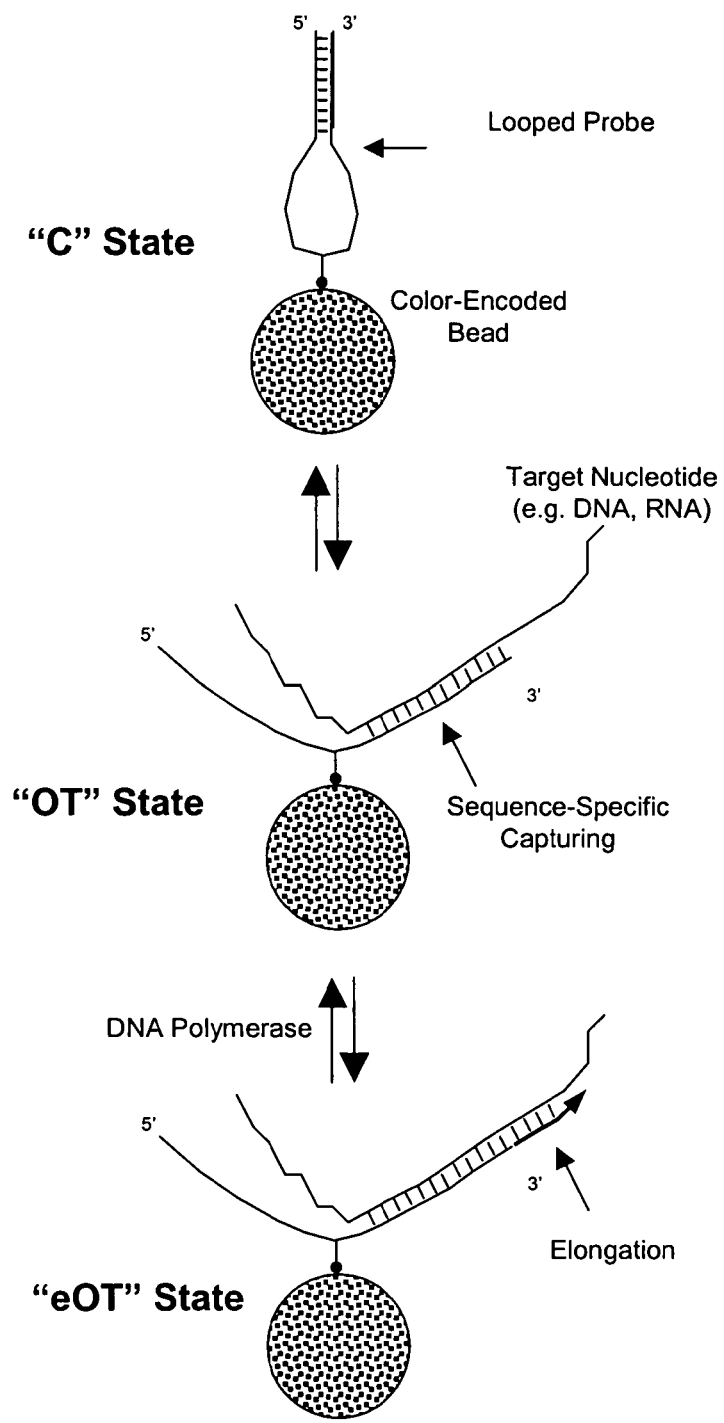
FIG. 2B is an illustration showing the target-mediated, enzymatic elongation of non-labeled looped probe.

1—Mathematical Description of Molecular Stringency: Competitive Target Capture

In general, the interaction of a looped probe with a target nucleic acid will be governed by a set of coupled equilibria between the non-fluorescent closed ("C") state, and the fluorescent open ("O") state and the fluorescent target-associated ("OT") state. Capture of a target nucleic acid is detected by way of detecting a transition from the C to the OT state. The O state, which is not associated with the target, contributes to a "background fluorescence". The equations below describe mathematically the corresponding coupled equilibria. The four input parameters are the initial looped probe concentration $[P]^0$, initial target concentration $[T]^0$, and the relevant equilibrium constants.

In the most general situation, the target is permitted to interact not only with the open but also directly with the closed state of the looped probe (in a displacement reaction) so as to form a probe-target complex. For molecular beacon probes in solution—beacons, in contrast to the looped probes considered here, are designed to form a probe-target complex by way of the loop sequence and thus do not impose molecular stringency—Bonnet et al. reported a mathematical model applicable under conditions of excess target (see Bonnet et al, Proc. Natl. Acad. Sci. USA Vol. 96, pp. 6171-6176, May 1999, Biophysics). Here, we consider the more general situation, i.e., that there is usually low concentration of target and excess probe, in assays using solid phase-immobilized probes to detect targets in solution.

Consider first looped probes, exposed to targets, the probes capable of adopting one of three states: (i) a duplex state (associated with target), (ii) a closed state (the complementary stem subsequences forming a duplex), and (iii) an open state, for example in the form of an open random coil (prevalent, for example, at high temperature). At equilibrium:

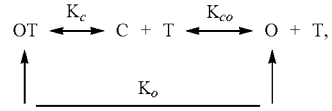

where OT is the looped probe-target duplex, C is the probe in its closed state, O is the probe in the form of a random coil, and T is the free target. The normalized fluorescence at a given temperature should be the sum of the contribution from each of the three states:

$$F = \alpha \frac{[OT]}{P^0} + \beta \frac{[C]}{P^0} + \gamma \frac{[O]}{P^0}$$

where $\alpha$, $\beta$, and $\gamma$ are the fluorescence quantum efficiency (QE) of the looped probe in each state, and $$P^0 = [OT] + [C] + [O]$$

$$T^0 = [OT] + [T]$$

The law of mass action gives the following expression for the equilibrium constants governing the dissociation of the looped probe:

$$K_c = \frac{[C] \cdot [T]}{[OT]},$$

$$K_{co} = \frac{[O]}{[C]},$$

$$K_o = \frac{[O] \cdot [T]}{[OT]}.$$

These affinity constants are related by the following relation:

$$K_{co} = \frac{K_o}{K_c}.$$

Two limiting cases of interest are:
Excess Probe, i.e., $P^0 \gg T^0$:
The fraction of probes in each state can be expressed in terms of the equilibrium constants, $K_c$ and $K_o$ as follows:

$$\frac{[OT]}{P^0} = T^0(P^0 + K_c + K_o)^{-1}$$

$$\frac{[C]}{P^0} = K_c(K_c + K_o)^{-1}$$

$$\frac{[O]}{P^0} = K_o(K_c + K_o)^{-1}$$

Thus, the total fluorescence intensity is:
$$F=\alpha T^0(P^0+K_c+K_o)^{-1}+\beta K_c(K_c+K_o)^{-1}+\gamma K_o(K_c+K_o)^{-1}.$$

Excess Target, i.e., $P^0 \ll T^0$:

The fraction of probes in each state again can be expressed in terms of the equilibrium constants, $K_c$ and $K_o$ as follows:

$$\frac{[OT]}{P^0} = T^0(P^0+K_c+K_o)^{-1}$$

$$\frac{[C]}{P^0} = K_c(T^0+K_c+K_o)^{-1}$$

$$\frac{[O]}{P^0} = K_o(T^0+K_c+K_o)^{-1}$$

Thus, the fluorescence intensity is:
$$F=[\alpha T^0+\beta K_c+\gamma K_o](T^0+K_c+K_o)^{-1}.$$

These equations may be simplified by assuming equality of quantum efficiencies (QE) in the duplex and open states, i.e., $\alpha \sim \gamma$, and negligible QE in the closed state, i.e., $\beta \sim 0$:

$$[OT] = \frac{(K_c+K_o)+P^0+T^0 \pm \sqrt{(K_c+K_o+P^0+T^0)^2 - 4P^0T^0}}{2} \quad (1)$$

Then, for the case of excess probe, i.e., $T^0 \ll P^0$:

$$[OT] = \frac{(K_c+K_o)^{-1}P^0T^0}{(1+(K_c+K_o)^{-1}P^0)}$$

and similarly, for excess target, i.e. $P^0 \ll T^0$:

$$[OT] = \frac{(K_c+K_o)^{-1}P^0T^0}{(1+(K_c+K_o)^{-1}T^0)}$$

Both expressions are equivalent to a Langmuir adsorption isotherm describing the capture of target to a probe-decorated solid phase in a process governed by a single effective affinity constant, $K_{eff}=(K_c+K_o)^{-1}$ The fraction of signal originating from the probe-target complex, compared to that originating from the open state of the probe, is given by:

$$\eta = \frac{[OT]}{[O]} = \frac{(K_c+K_o)}{K_o}\left\{\frac{[OT]}{P^0-[OT]}\right\}$$

Simplified Model: No Displacement—

A similar result also is obtained by considering the target to interact only with the open form of the looped probe in accordance with a coupled equilibrium:

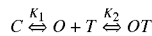

where $K_1$ and $K_2$ are the association equilibrium constants, namely:

$$K_2 = \frac{[OT]}{(T^0-[OT])[O]} \text{ or,}$$

-continued $$[OT] = \frac{K_2 T^0[O]}{1+K_2[O]}$$

Similarly $$K_1 = \frac{[O]}{(P^0-[O]-[OT])} \text{ or,}$$

$$[O] = \frac{K_1(T^0-[OT])}{(1+K_1)} = \delta(T^0-[OT]) \text{ where}$$

$$\delta = \frac{K_1}{(1+K_1)}$$

These two algebraic equations yield:

$$K_2\delta[OT]^2 - (1+K_2\delta T^0+K_2\delta P^0)[OT] + K_2\delta T^0 P^0 = 0 \quad (2)$$

$$[OT] = \frac{(1+K_2\delta T^0+K_2\delta P^0) \pm \sqrt{(1+K_2\delta T^0+K_2\delta P^0)^2 - 4(K_2\delta)^2 P^0 T^0}}{2K_2\delta}$$

$$[OT] = \frac{\left(\frac{1}{K_2\delta}+T^0+P^0\right) \pm \sqrt{\left(\frac{1}{K_2\delta}+T^0+P^0\right)^2 - 4T^0P^0}}{2}$$

Then, for excess probe, i.e., $P^0 \gg T^0$:

$$[OT] = \frac{\delta K_2 P^0 T^0}{(1+\delta K_2 P^0)}$$

and similarly, for excess target, i.e. $P^0 \ll T^0$:

$$[OT] = \frac{\delta K_2 P^0 T^0}{(1+\delta K_2 T^0)}$$

Both expressions are equivalent to a Langmuir adsorption isotherm describing the capture of target to a probe-decorated solid phase in a process governed by a single effective affinity constant, $K_{eff}=\delta K_2$ The fraction of signal originating from the probe-target complex, compared to that originating from the open state of the probe is given by:

$$\eta = \frac{[OT]}{[O]} = \delta\left\{\frac{[OT]}{P^0-[OT]}\right\}$$

Both models thus generate similar mathematical expressions for [OT], namely:

$$[OT] = \frac{1}{2}\left\{(K_{eff}+T^0+P^0) - \sqrt{(K_{eff}+T^0+P^0)^2 - 4T^0P^0}\right\}$$

where $K_{eff}$ represents an association equilibrium constant governing the reaction $P+T \Leftrightarrow OT$, between any of the states of the probe, P, and the target-associated state, and $P^0$ and $T^0$ respectively denote the initial concentrations of the probe and target. For the general model, $K_{eff}=(K_c+K_p)^{-1}$ and for the simplified model, $K_{eff}=K_1K_2/(1+K_1)$.

Both models likewise generate similar expressions for the parameter $\eta$, namely:

$$\eta = \lambda \left\{ \frac{[OT]}{P^0 - [OT]} \right\}$$

where $\lambda$, for the general model, is given by: $\lambda=(1+K_c/K_o)$, and for the simplified model is given by $\lambda=(1+K_1)/K_1$.

Under conditions of low coverage, $[OT]/P^0 \ll 1$, $\eta$ increases linearly with $[OT]$ which, in this regime, is in turn linearly dependent on $K_{\it eff}$. Hence, in this low coverage regime, an increase in $K_{\it eff}$ reflecting choice of ionic strength and/or temperature, will lead to an increase and hence detection sensitivity. This can be brought about by a choice in buffer conditions such that affinity $K_1$ or $K_{co}$ decreases, which destabilizes the O state in favor of the OT state.

Probability of Target-Probe Encounter: Solution Vs Solid Phase—

Figure 3:
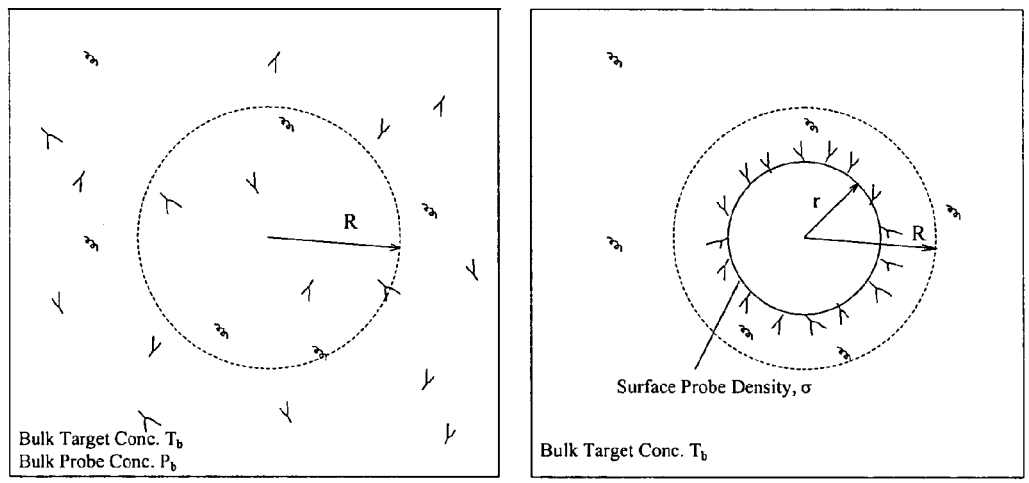
FIG. 3 is an illustration comparing a volume element of solution containing uniformly distributed capture probes, and a volume element containing a microparticle and capture probes confined to a shell.

For given target concentration, the probability of a target molecule encountering a probe is determined by the effective concentration of probes. With reference to FIG. 3, consider a test sphere of a radius r and a concentric shell of radius $R=r+\delta$ the sphere displaying probes at a density $\sigma \sim P^0/r^2$. The effective probe concentration within the shell is given by $$[P_s] = \frac{3\sigma \cdot r^2}{R^3 - r^3}.$$

Letting R decrease toward r, that is, in the limit $\delta \to 0$, the local probe density approaches the limit $$[P_s] = \frac{\sigma}{\delta};$$

in this limit, probes may be viewed as "condensed" on the bead surface.

For example, given a bead of diameter 3.2 μm and a typical value of $P^0$ of $10^6$ per bead, $\sigma \sim 10^5$ μm$^{-2}$. The effective probe concentration within a shell of dimension $\delta=0.1$ μm is thus:

$[P_s] \approx 3 \times 10^5$ [μm$^{-2}$]/0.1 [μm]$\approx 3 \times 10^6 \times 10^{-24}$[M]/$10^{-15}$
[L]~3 mM.

Typical conditions for target capture in solution involve a choice of probe concentration equal to the maximal anticipated target concentration. Assuming a dynamic range of 2 orders of magnitude, the probe concentration will exceed the lowest detectable target concentration by not more than 2 orders of magnitude. Thus, in order to permit detection of target at a concentration of 10 nM (see Example 1), a typical probe concentration will be 1 μM. The effective probe concentration associated with the bead thus exceeds, by at least 3 orders of magnitude, that typically encountered in solution. Accordingly, as a target approaches the solid phase carrier surface, it encounters probes with a far higher probability than that governing such encounters in solution, and this translates into a correspondingly higher local concentration of probe-target complexes. This invention discloses, immediately, below, a hopping model permitting the target to interact, during each encounter with the bead surface, with not one, but multiple probes, thereby extending its residence time near the surface.

Enhanced Detection Sensitivity: Target "Hopping" and Recapture—

Figure 4:
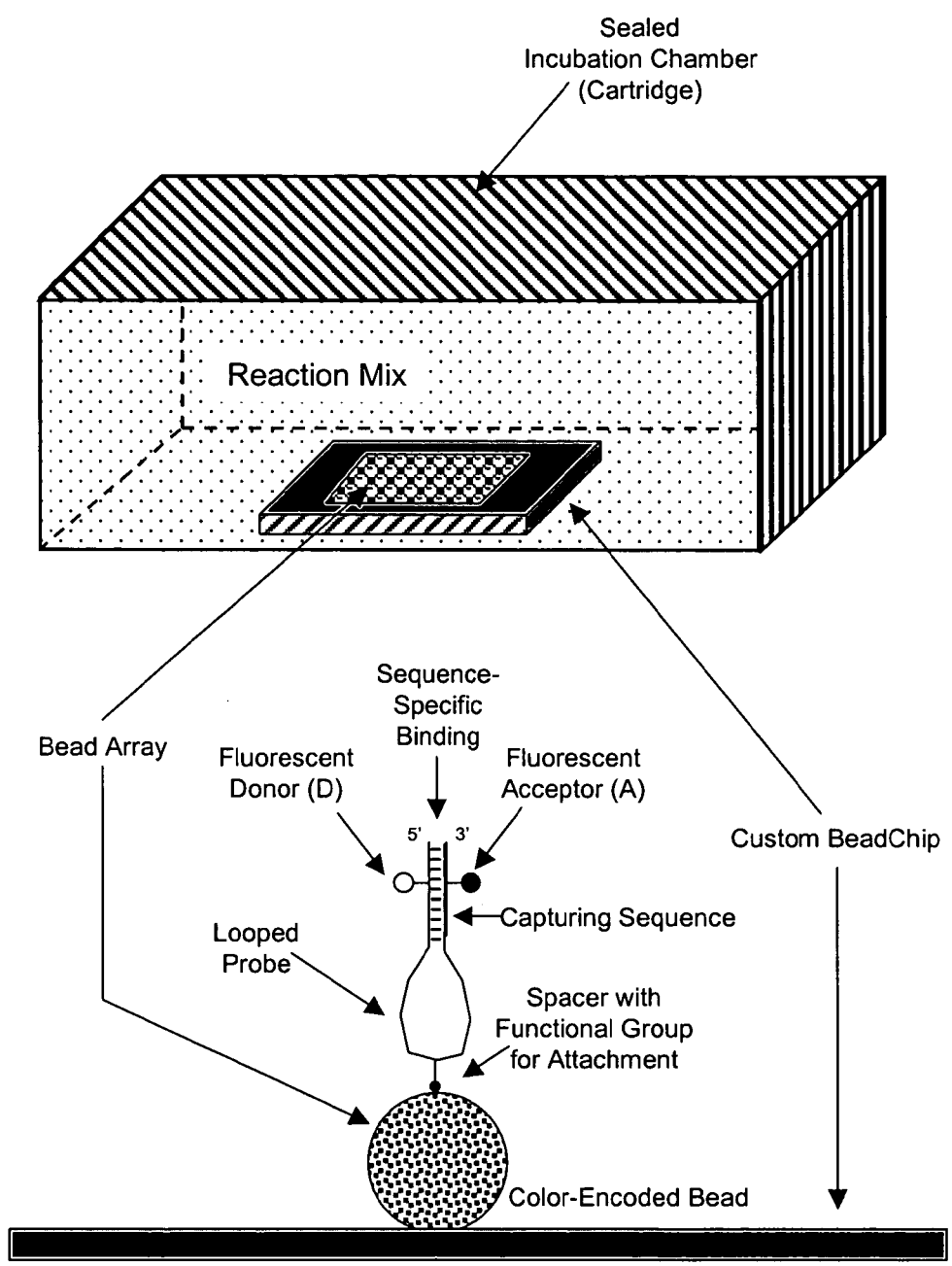
FIG. 4A is an illustration showing the configuration of a homogenous assay performed using looped probes displayed on a pre-assembled random array of encoded beads.
FIG. 4B is an illustration showing an arrangement for performing a homogenous assay using looped probes displayed on a pre-assembled random array of encoded beads, where the array is mounted on an insert at the tip of a reaction tube and imaged in an inverted imaging arrangement.
Figure 4B:
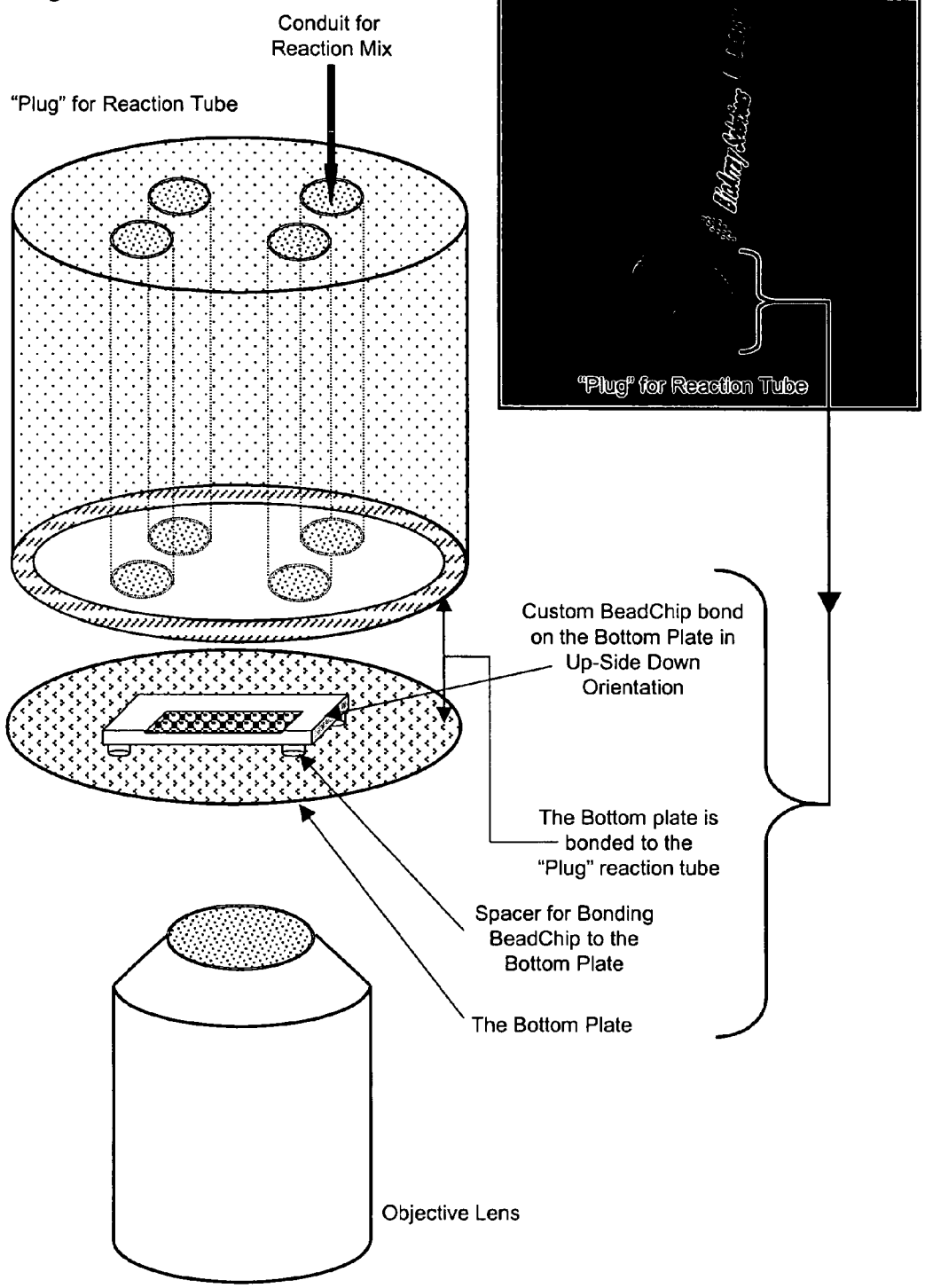
Figure 5:
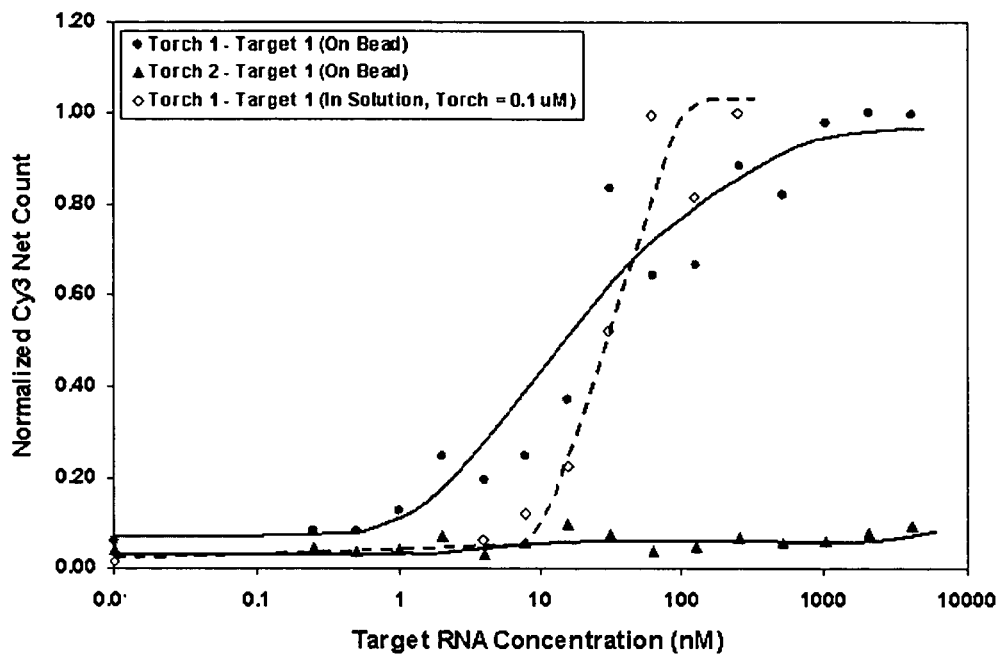
FIG. 5 is a representation showing the capture of RNA target to bead-displayed self-complementary capture probes in homogeneous BeadChip assays.
Figure 5:
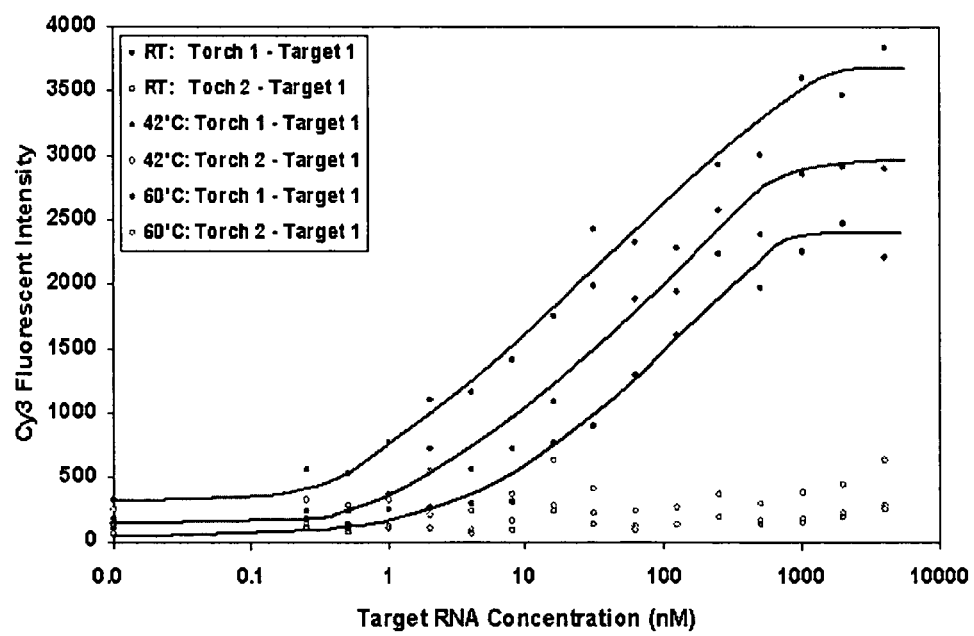

Experimental observations, described in greater detail in Example 1 and in FIGS. 4 and 5, especially in the upper panel of FIG. 5, for a looped probe attached by its loop subsequence to a microparticle ("bead"), indicate the response to display, in the regime of low target concentration, a substantially enhanced detection sensitivity as compared to the response of that probe in solution.

Figure 6:
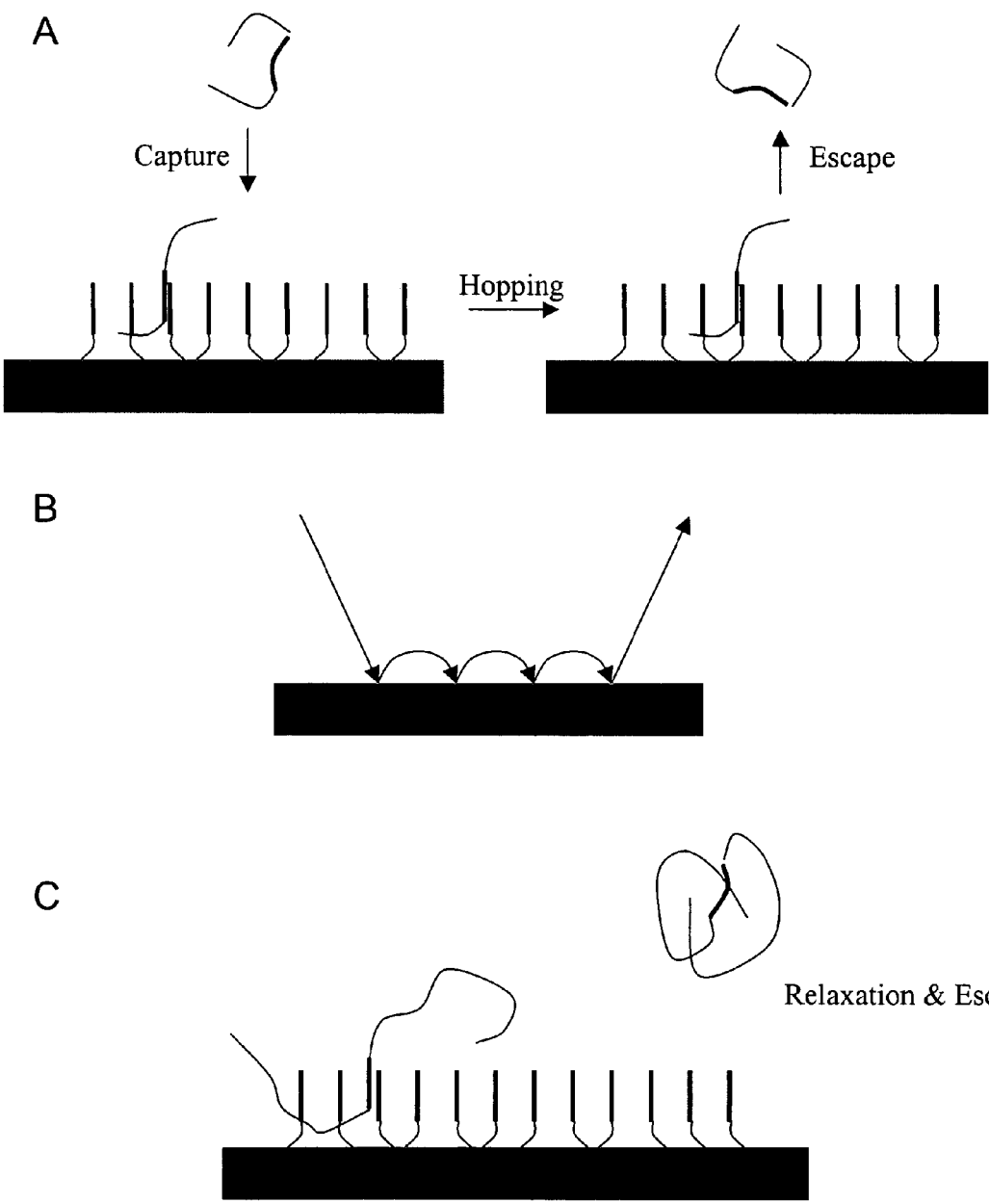
FIG. 6 is an illustration of target "hopping" process and the escape process with concomitant shape relaxation.

The enhancement is attributed to target "hopping" from occupied to nearby unoccupied capture probes (see FIG. 6A, B). That is, targets execute random walks (of varying extent) on the surface by hopping from site to (unoccupied) site. If "hopping" can occur sufficiently rapidly so as to leave the target conformation essentially unchanged and thus "primed" for recapture (FIG. 6A), this process will increase the residence time of the target at or near the surface. Denoting by $\tau$ the characteristic relaxation time of the target conformation, from its constrained state it must adopt for association with the carrier-displayed probe, to the unconstrained state it adopts as it "escapes" into the bulk solution (FIG. 6C), the distance, $d_{NN}$, between any occupied probe site and the nearest unoccupied site(s) so as to permit (random) "hopping" on a timescale $\tau_h < \tau$. Denoting by $\mu_h$ a characteristic hopping mobility, and corresponding diffusivity $D_h = (kT/M)\mu_h$, M representing the mass of the target molecule, this condition translates into $d_{NN}^2 < D_h \tau$ or, for the probe density, $\sigma \sim d_{NN}^{-2} > 1/D_h \tau$.

Phenomenologically, the increase in target residence time manifests itself in the form of a reduction in the observed rate of dissociation. The ratio, $k_d/k_{d0}$, of the observed to the "intrinsic" rate decreases with increasing probability of a target completing a "hop" from its current probe site to a nearby (unoccupied) probe site, and this probability, $\Theta$, in turn increases with the number of probes $P^0$ provided on the surface, and with the unoccupied fraction, $1-\Gamma$, of those probes. Thus, $k_d$ may be represented in a form $k_d = k_{d0} \lfloor 1 - \Theta(P^0, 1-\Gamma) \rfloor$ where $\Theta(P^0, 1-\Gamma)$ represents the probability of target recapture at a site close to the site of release; $\Theta(P^0, 1-\Gamma)$ will be a monotonically increasing function of $P^0$ and $1-\Gamma$, and $\max(\Theta) \leq 1$.

Solving for $\Gamma$, from the detailed balance equation, $k_a(1-\Gamma,)T_s = k_d \Gamma$ . . . yields:

$$\Gamma \equiv \frac{[PT]}{P^0} = K_0 T_s (1 + K_0 T_s - \Theta(P^0, 1 - \Gamma))$$

where $K_0 = k_a/k_{d0}$ represents the affinity constant observed in the absence of target retention; in the limit of low target concentration, or small affinity constant, $\Gamma = KT_s$.

The observed affinity constant, $K = K_0 [1 - \Theta(P^0, 1-\Gamma)]^{-1}$.

is enhanced at low target concentration, reflecting the large fraction of capture sites available to each target molecule; K decreases toward its "intrinsic" value at high coverage. Regardless of its detailed form, the recapture probability function, $\Theta(P^0, 1-\Gamma)$, relates an increase in observed affinity to an increase in total surface probe density and/or decrease in coverage. By enhancing the observed affinity, this cooperative effect arising from target hopping between densely grafted probes on a solid surface favors complex formation and thus accounts for an enhanced sensitivity. The arguments advanced herein are not limited to the self-complementary ("looped") probes employed here, and will apply to any target (or ligand) capture to solid-phase displayed capture probes (or receptors) at low target (or ligand) concentration.

Interfacial Polarization—

At high stringency, capture especially of short targets will occur within a polarized interfacial region of elevated ionic strength, and hence under conditions of lower stringency as compared to conditions in the bulk solution. For example, for a 50-mM bulk NaCl concentration, this interfacial region extends to a characteristic length $1/\kappa \sim 30$ Å beyond the surface of the solid phase carrier. Given the increased effective target concentration, this will further stabilize the OT state, a conclusion which also follows from the analysis of the mathematical description described above (see Eq 1). Under these conditions, an effect such as a counterion-mediated attraction of short range (Ha & Liu, Phys Rev Letts. 79, pp 1289-1292 (1997)) may contribute to target retention within the interfacial region.

Expanded Dynamic Range—

The experimental observations described in the Examples below also indicate the response of looped probes anchored to a solid surface to display a more than two-fold expansion of dynamic range as compared to that observed in solution.

At typical grafting densities of at least $10^5$ probes per bead, a solid phase assay, especially in the regime of low target concentration, corresponds to conditions of excess probe. Under the assumption, $\alpha \sim \gamma$, $\beta \sim 0$, discussed above, and under the further assumption $K_c \gg K_o$, the absolute fluorescence intensity assumes the form:

$$F_{ab} \alpha P^0 T^0 (P^0+K_c)^{-1} = \alpha T^0 (1+K_c/P^0)^{-1}$$

This expression, describes an increase in the intensity of fluorescence emitted by looped probes with increasing probe density. That is, the response, given by the slope, $\alpha(1+K_c/P^0)^{-1}$, in fluorescence intensity as a function of variations in target concentration, will affect the intensity of emitted fluorescence. For example, under conditions described in Example 1, $K_c \approx 0.1$ μM, so that, if the grafting density, and hence $P^0$ is varied from (an equivalent of) 10 nM to (the equivalent of) 10 mM, the response in fluorescence signal intensity can be varied over an order of magnitude, from $0.1\alpha$ to $\alpha$.

The broadening in the response is reminiscent of that observed when comparing the response of a polyclonal antibody to that of a monoclonal antibody (Tarnok, Hambsch, Chen & Varro, Clinical Chemistry 49, No. 6, pp 1000-1002, 2003). However, as described herein, anchored looped probes, grafted at high density, also display an enhanced detection sensitivity at low target concentration. This effect, which has not been described in connection with immunoassay designs replacing a monoclonal capture antibody by a polyclonal capture antibody, is attributed here to an enhanced observed ("effective") affinity at low coverage in accordance with a target hopping model.

In accordance with the target hopping model, a cooperative effect related to probe grafting density enhances the affinity observed at low coverage, thereby further contributing to the heterogeneity in the response in a manner that is favorable to generating an expanded dynamic range of target detection. At low target concentration, the response is dominated by the enhanced affinity arising from target retention near the surface, and at high target concentration, the response is dominated by the low affinity associated with low grafting density. That is, the expanded dynamic range reflects the contributions of enhanced sensitivity at low coverage, and those of solid phase carriers of lower affinity at high coverage.

2—Formation of eOT State: Enhancing Operating Range and Detection Sensitivity—

The use of a looped probe calls for operation within a range of optimal stringencies that is determined by a trade-off between detection sensitivity and specificity. Conditions of low stringency will stabilize the C state, thereby rendering target capture more difficult and reducing detection sensitivity. Conversely, conditions of high stringency will destabilize both the C state and the OT state, as evident from the results of the detailed mathematical description provided herein above, thereby reducing specificity: in the extreme, the open state of the probe will produce fluorescence even in the absence of target.

Optimization of specificity generally will dictate selection of an operating temperature near the melting temperature of the relevant probe-target complex. However, as this choice also reduces the stability of the probe-target complex, it reduces detection sensitivity. Conversely, a choice of lower stringency increases the sensitivity, but compromises the specificity of the response. When detection of target by capture to looped probes is to be performed concurrently with enzymatic target amplification (or other enzyme-catalyzed target manipulation) in a homogeneous format, or subsequent to such manipulations, but without intervening separation step, in a "single-tube" format, the choice of optimal stringencies may be further constrained. In practice, high stringency is preferred: for example, the conditions of Example 1, involving the formation of a duplex of 20 base pairs, provide for 50 mM salt and an operating temperature of 42 C.

Optimal stringencies generally will depend not only on specific capture probe sequences, but on target configuration and/or length, and the task of identifying the operating range of stringencies in a multiplexed assay thus becomes increasingly difficult, given the dispersion of the melting curve profiles of a set of different probe-target complexes under given assay conditions. The design of a multiplexed assay format calling for the concurrent detection of multiple targets by capture to matching probes, will thus further restrict the choice of optimal stringencies which depend on the stability of individual probe-target complexes.

Thus, target-mediated elongation of (the 3'terminal subsequence of) a self-complementary probe provides a method of stabilizing probe-target complexes by converting the OT state into the elongated ("eOT") state and thereby a method of expanding the operating range particularly of multiplexed nucleic acid detection while simultaneously enhancing the sensitivity of detection. Elongation may be performed using DNA target and a DNA polymerase or RNA target and a Reverse Transcriptase (RT), as described in the co-pending application included herein by reference. The probe is constructed so as eliminate "self-priming", either by providing strictly blunt ends of the stem, or preferably by providing an "overhanging" 3'terminus.

Expanding the Operating Range—

Figure 7A:
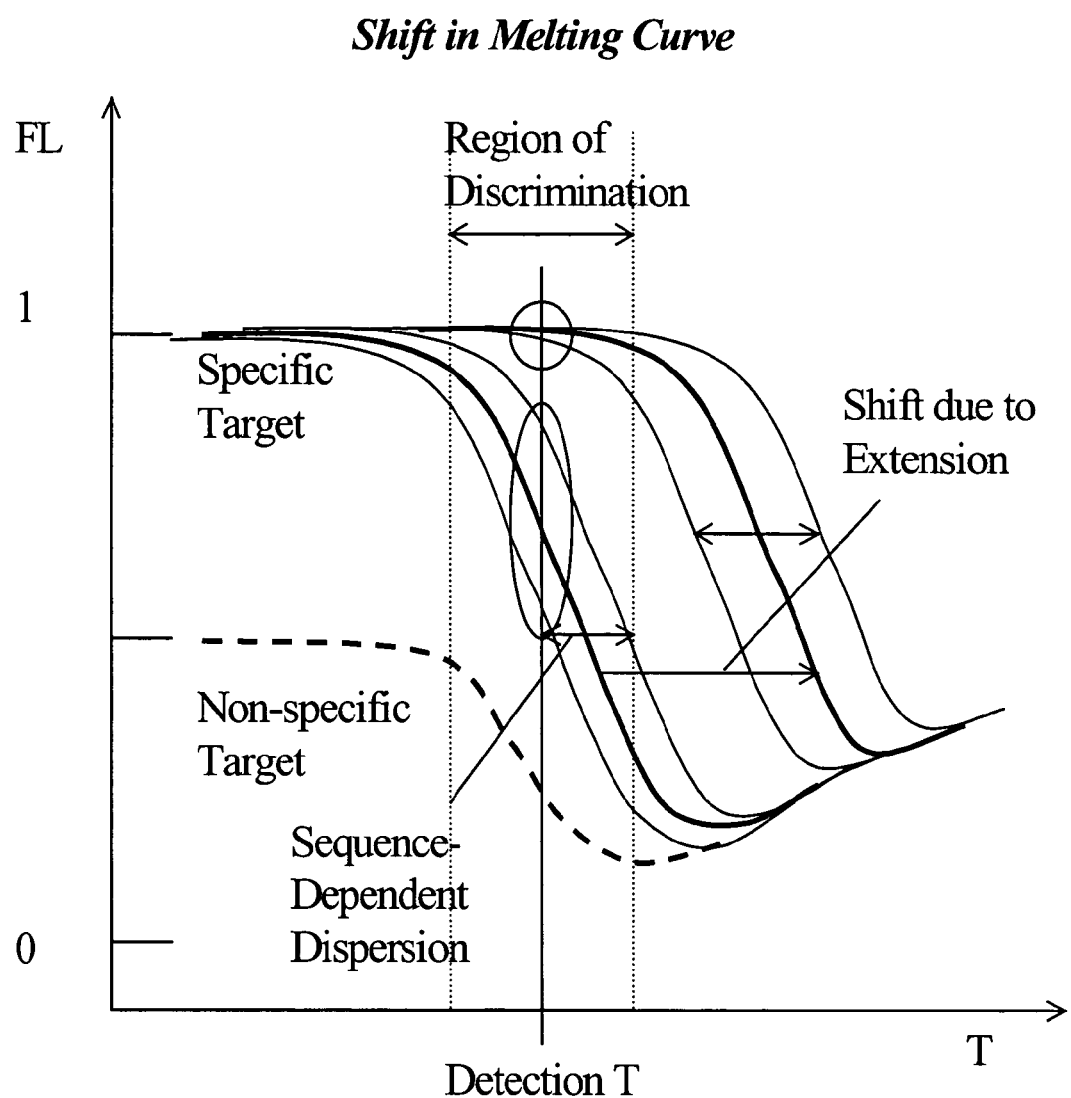
FIG. 7A is an illustration of the effect of probe elongation on the melting curves of several probe-target complexes.
Figure 7B:
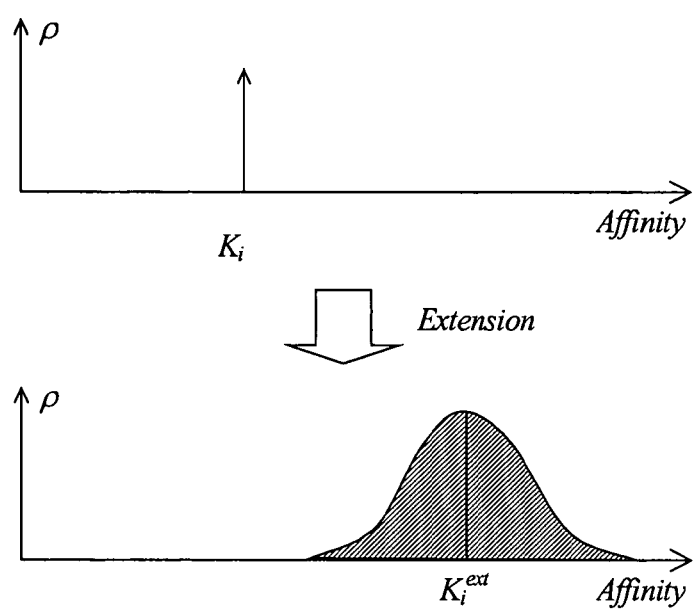
FIG. 7B is an illustration of the effect of randomly aborted probe elongation on the distribution of affinity constants.

The enhanced thermodynamic stability of the eOT state manifests itself in a shift to higher temperature of the melting curve: generally, the longer the template, the larger shift. In contrast, since the 5' terminal subsequence of the probe remains unmodified, the C→O transition follows its original melting curve. In a multiplexed assay, this shift of the dispersive portion of the melting curves of different probe-target complexes to higher temperature, renders the system more forgiving in terms of selecting a high operating temperature: as illustrated in this situation FIG. 7A, the ability to operate at high temperature ensures high stringency and hence specificity, and the ability remain outside of the range of dispersion simultaneously ensures high sensitivity. Non-uniform probe elongation, as a result of randomly aborted probe elongation reactions, would produce a polydisperse length distribution and would further broaden this distribution of affinity constants. Such an increase in heterogeneity will manifest itself in an increase in the dispersion of the (shifted) melting curves (see FIG. 7B); that is, randomly aborted elongation reactions provide a means of expanding the dynamic range of the assay.

Enhancing the Sensitivity—

The enhanced stability of the eOT state also translates into enhanced detection sensitivity, as a result of shifting the equilibrium of the competitive probe-target interaction to the duplex state by converting OT states, essentially irreversibly, into stable eOT states. Phenomenologically, this conversion corresponds to a a reduction of the observed rate of dissociation, and corresponding increase in the observed affinity of the probe-target interaction: to the extent that it is irreversible, this process, given sufficient time, will consume all available target.

The enhancement in detection sensitivity afforded by generation of the (essentially irreversible) eOT state is particularly effective when operating in a regime of stringency permitting only the transient formation of an OT state. Random fluctuations producing the transient formation of a probe-target-enzyme-substrate intermediate will mediate the (essentially) irreversible conversion of a fraction of this intermediate OT state into an eOT state, leading, over time, to accumulation of eOT state and depletion of target. The "zippering-up" of the intermediate OT state producing the eOT state, akin to the turn of a ratchet, permit operation in a regime of low stringency without loss of detection sensitivity.

3—Allele-Specific Detection and Phasing

As with allele-specific detection of nucleic acids generally, looped probes may be used to advantage in connection with Elongation-mediated Multiplexed Analysis of Polymorphisms (eMAP™; see U.S. application Ser. No. 10/271, 602). In this application, the use of a looped probe has the additional benefit of permitting control of molecular stringency so as to improve allele discrimination by target capture. In particular, eMAP using looped capture probes which simultaneously serve as elongation primers permit the application of phasing, either in the mode described in detail in U.S. application Ser. No. 10/271,602 (incorporated by reference), or by combining the stringent control of annealing conditions afforded by the design of specific stem subsequences with allele-specific elongation of a 3'-terminal subsequence whose 3' terminus is designed not to display complementarity with the 5'-terminal subsequence so as to eliminate the possibility of self-priming.

Figure 8:
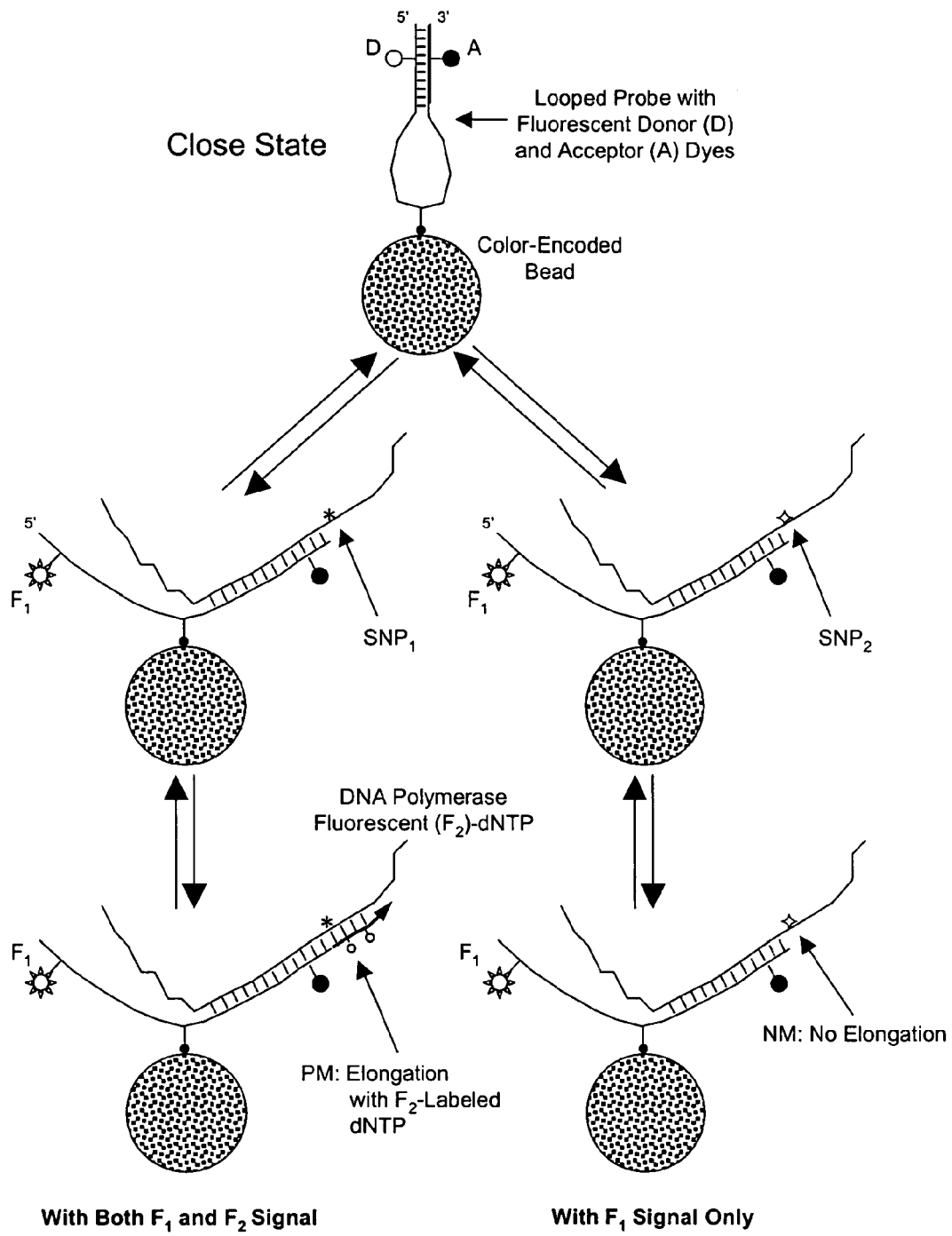
FIG. 8 is an illustration of phasing, performed by elongation of allele-specific looped probes.

That is, as illustrated in FIG. 8, the configuration of a first variable site, located within the portion of the sequence capable of annealing to the 3'-terminal subsequence of the probe is detected by preferential capture of the matching allele, and the configuration of a second variable site, located in juxtaposition to the 3'terminus (or proximal position) of the probe, is detected by elongation (or lack thereof). Elongation products may be formed under conditions permitting incorporation of fluorescently labeled dNTPs or may be formed with unlabeled dNTPs and decorated by a fluorescently labeled hybridization probe; such a decoration probe can be designed to be directed to an additional polymorphic site of interest located in the elongated probe sequence.

Example I

Homogeneous Beadchip Assay Using Looped Probes

A homogenous BeadChip assay format, shown in FIG. 1, was implemented by providing a variable gap configuration set to a large value during target capture and a smaller value during recording of assay images from a random encoded array of beads displaying self-complementary probes as well as positive and negative controls. The reaction volume was sealed by encapsulation of the reaction with mineral oil (from Sigma-Aldrich).

BeadChips were prepared to contain a random array composed of 4,000 beads of four types of color-encoded microparticles ("beads") on a 375-µm thick <100> n-type Silicon substrate. Color-coding was achieved by staining the beads in accordance with a solvent tuning method described in U.S. application Ser. No. 10/348,165 (incorporated by reference). Stained beads were functionalized by covalent attachment of streptavidin to permit subsequent attachment of biotinylated self-complementary ("looped") probes, illustrated in FIG. 1.

One probe, displayed on one type of bead, contained a 20-nt capture sequences specific to a 20-mer single-stranded target; the other probe contained an unrelated 20-mer sequence. Three type of beads were respectively functionalized with a target-specific ("matched") probe, a mismatched probe serving as a negative control, and a biotinylated and Cy3-modified oligonucleotide ("A10") serving as an intensity reference; a fourth type of bead, left unfunctionalized, was added to dilute the array composition. BeadChips were affixed to glass substrates using an epoxy adhesive ("Loctite") and a polydimethylsiloxane (PDMS) spacer, either 400 µm or 1,000 µm in thickness, was cast; PDMS conforms well to flat surfaces and provides a reliable seal, given its negligible thermal expansion up to 100° C. Two 400-µm spacers were placed adjacent to the mounted BeadChip, and two 1000-µm spacers were placed next to the 400-µm spacers; a glass coverslip of 0.15 mm thickness was cut to fit the separation of the 1000-µm spacers.

To perform the assay, 1.5-µl of reaction mix containing specific target at a particular concentration was pipette-transferred to the chip surface; the reaction volume was closed by fixing the coverslip via two PDMS pads placed onto the 1,000-µm spacers, and transferring 5-µl of mineral oil into the gap; capillary forces ensure that the oil quickly encircles and isolates the reaction volume. After completion of the reaction, the coverslip was shifted so as to come to rest on the 400-µm spacers to form a 25-µm gap for optical interrogation.

The result of titrating a 20-mer RNA target on a Beadchip using this setup is shown in FIG. 5A at a temperature of 42 C and in FIG. 5B at two additional incubation temperatures, followed by imaging at room temperature. Fluorescence intensity readings, normalized using the A10 fluorescence, are shown along with normalized data recorded from the same assay performed in solution, using a fixed looped probe concentration of 0.1 µM. Compared to the solution response, the reaction with the bead-displayed probes displays a much broader detection dynamic range of target (3 logs) and substantially enhanced sensitivity at low target concentration.

Example 2

Homogenous Assay in Suspension of Encoded Beads

Figure 9:
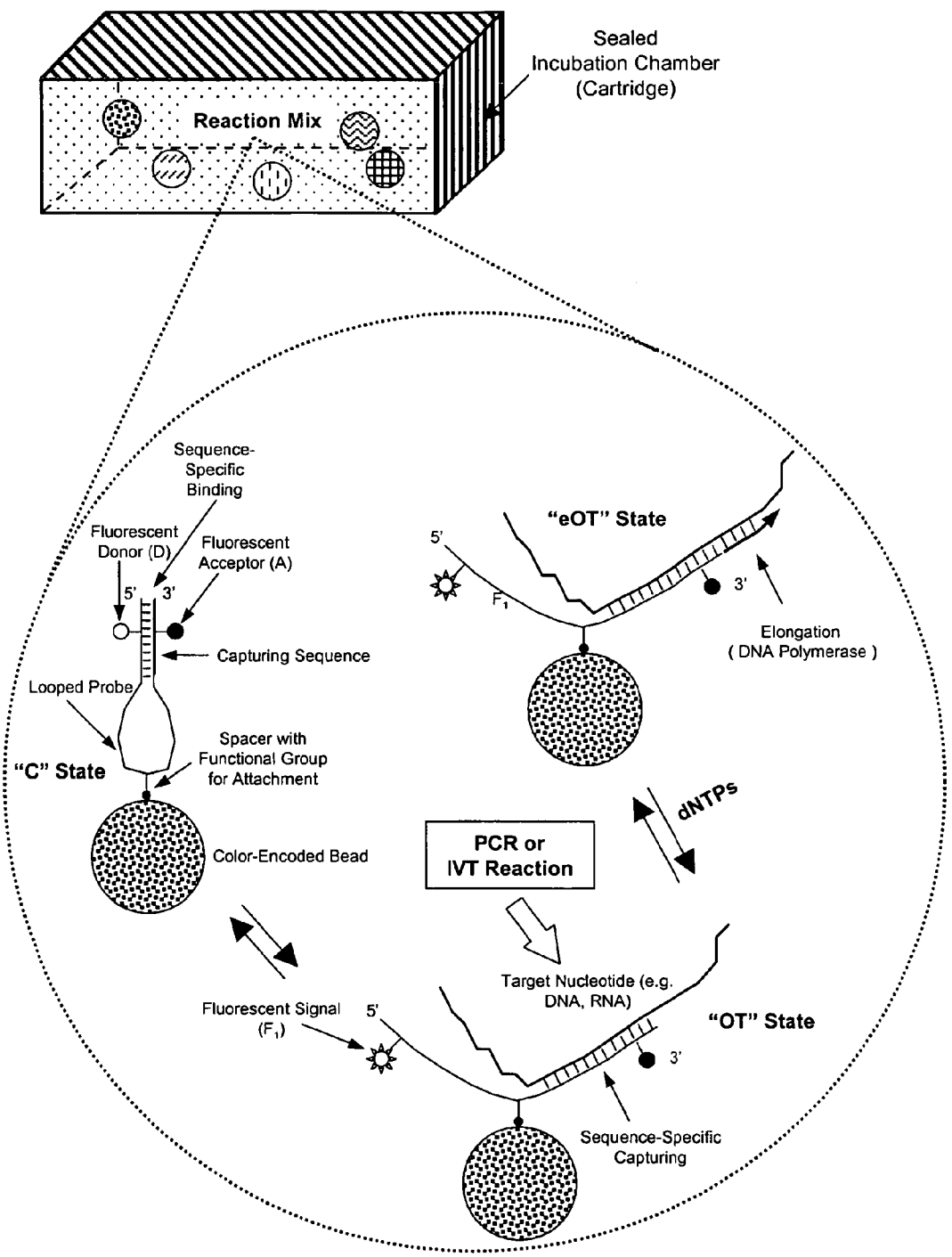
FIG. 9 is an illustration showing the configuration of a homogeneous assay performed using with labeled looped probes displayed on encoded suspended beads.
Figure 10:
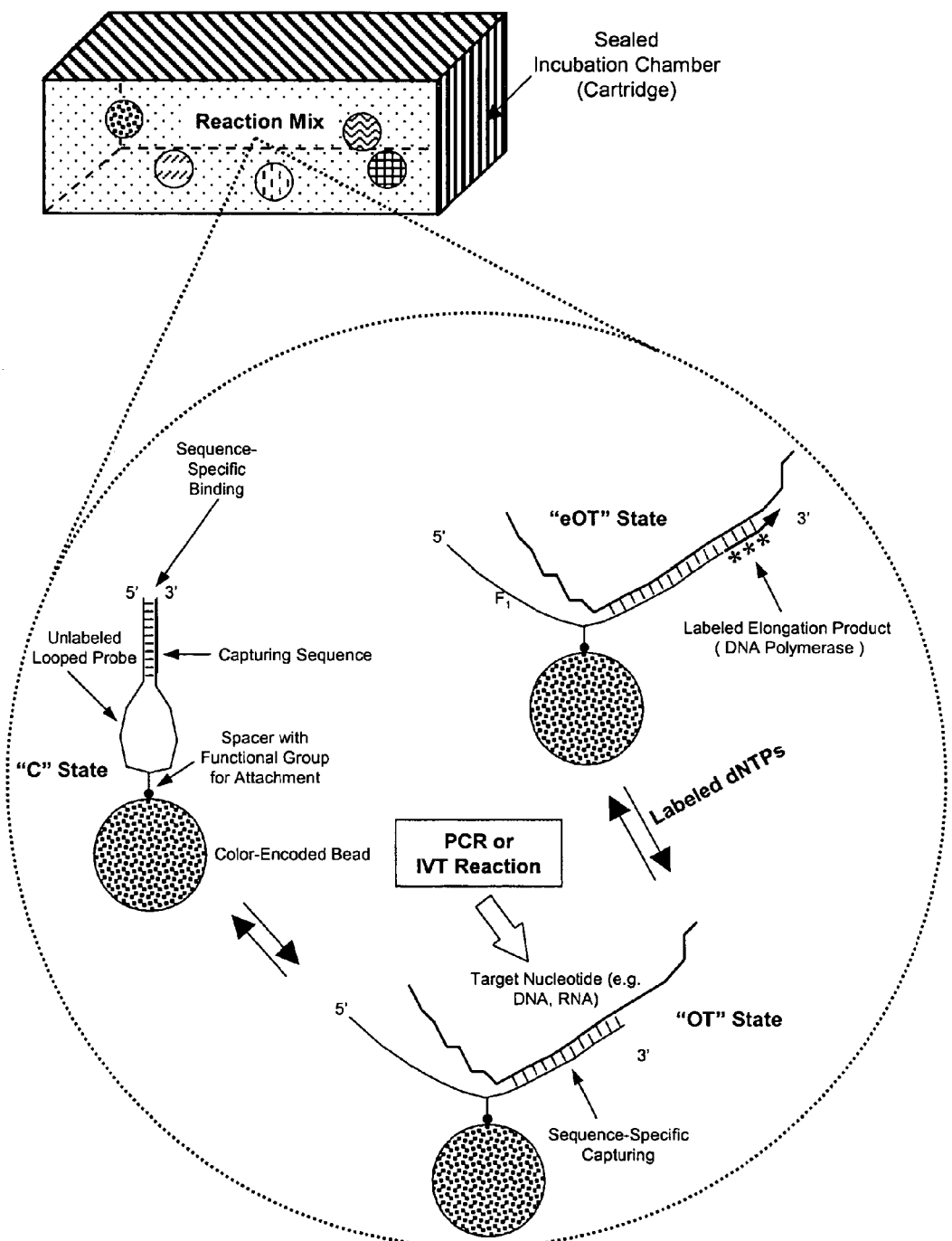
FIG. 10 is an illustration showing the configuration of a homogeneous assay performed using with non-labeled looped probes displayed on encoded suspended beads.

The looped-probe design also can be used in a homogenous format with encoded beads in suspension, as described in U.S. Pat. No. 6,251,691; U.S. application Ser. No. 10/204,799 (incorporated by reference). As shown in FIG. 9, a reaction mixture in a sealed incubation chamber, or cartridge, may contain T7-tagged DNA template, components for in-vitro transcription reaction such as a T7 RNA polymerase, well known in the art, and looped-probe functionalized color-coded beads, each color corresponding to a unique capture probe sequence. Preferably, encoded magnetic beads are used (see U.S. application Ser. No. 11/218,838), and a random array of such beads is assembled in real time following completion of the assay, as described in U.S. Pat. No. 6,251,691; U.S. application Ser. No. 10/204,799.

Two sets of magnetic beads (Spherotech, 4.10 µm in diameter, p~1.13 g/ml), one encoded with a green dye by solvent-tuning (REF—Solvent Tuning), the other left uncolored, are covalently functionalized with Strepavidin for attachment of a biotinlyated looped probe. One probe, displayed on the green beads, contains a 10-nt capture sequence specific to a 20-mer HIV single-stranded target; the other probe contains a 10-nt sequence unrelated to HIV. The looped probes are labeled with a Cy3 fluorescence dye on the 5'-terminal subsequence and a Blackhole quencher on the 3'-terminal subsequence Buffer containing all the reaction ingredients is adjusted in density by properly mixing with 20% Ficoll PM70 separation medium (Amersham) in D2O (Aldrich, ρ~1.18 g/ml, η~10 cp). The reaction suspension is then brought to 0.25% solid content.

In-vitro transcription is performed in the sealed chamber, or in a sealed cartridge, containing suspended beads (see also the detailed descriptions in the co-pending application included herein by reference). The reaction is initiated by raising the temperature to a predetermined value optimizing the efficiency of the T7 RNA polymerase; the "hot start" mechanism, well known in the art, also may be employed to initiate the reaction.

Real-Time Array Assembly and Detection—

The cartridge is placed into a magnetic field configuration designed to permit the formation of a random array of beads. Beads are first magnetically trapped at the semiconductor surface and the reaction buffer exchanged for assembly buffer, previously disclosed, preferred for the subsequent step: an AC voltage (typically <1 Vpp, <1 kHz) is applied to the electrodes and a spot on the substrate, defined by an aperture in the projection optics, is illuminated (typically with a power of 30 mW/mm$^2$ generated by a 12V/100 W Halogen Lamp), and a converging electrokinetic flow directed toward the illuminated spot is induced near the semiconductor surface. Under the influence of both electrokinetic and magnetic-dipole-repulsive forces, beads gather in the illuminated region but remain separated from each other. Finally, beads are "annealed" into a dense-packed ordered planar assembly. Images are then recorded with a CCD camera (Apogee).

In an alternative arrangement, the fluorescence signal associated with the open state of the looped probe may be detected by inserting the reaction mix into a flow cytometer which also permits decoding of the beads and hence determination of sequences corresponding to each assay signal.

Example III

Homogeneous Binding Assay in Suspension Using Looped Probes Immobilized on Magnetic Beads Looped probes were immobilized on color-encoded magnetic microparticles ("beads") for use in a homogeneous binding assay. Briefly, magnetic beads of ~4 micron diameter were synthesized by standard methods and color-encoded as set forth in U.S. application Ser. No. 10/348,165, incorporated by reference. Next, encoded beads were modified by covalent attachment of Neutravidin to epoxy groups on the beads to permit: attachment of a "perfect-match (PM)" biotinylated looped probe, a "no-match (NM)" biotinylated looped probe, and a biotinylated positive control, in the form of a Cy3-labeled oligonucleotide.

As in the previous examples, looped-probes contain a donor dye and an acceptor dye at their respective 5' and 3' ends. Aliquots of probe-decorated, encoded magnetic beads were pooled in one test tube for determination of RNA target concentrations.

Figure 11:
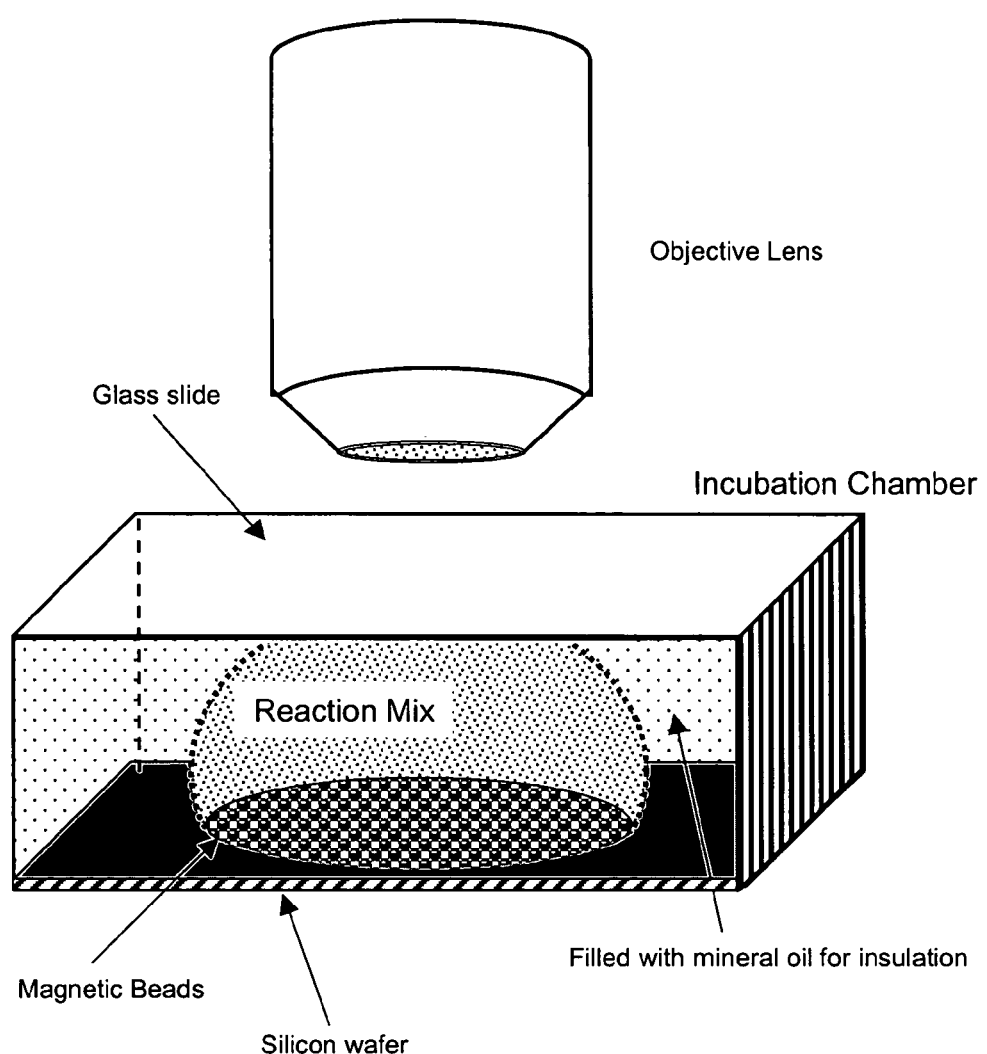
FIG. 11 is an illustration of into an incubation chamber in place on a silicon wafer.

To determine the response of the probes, target RNAs were serially diluted (1:2) in reaction buffer (50 mM Tris (pH 8.0), 0.1 mM EDTA, 50 mM NaCl, 0.2% Tween 20) and were then each incubated with an aliquot of pooled magnetic beads in a test tube. Following incubation for 10 min at room temperature, a 0.5 µl aliquot of each bead suspension was transferred—without washing—into an incubation chamber on a silicon wafer (FIG. 11) for image acquisition.

Figure 12A:
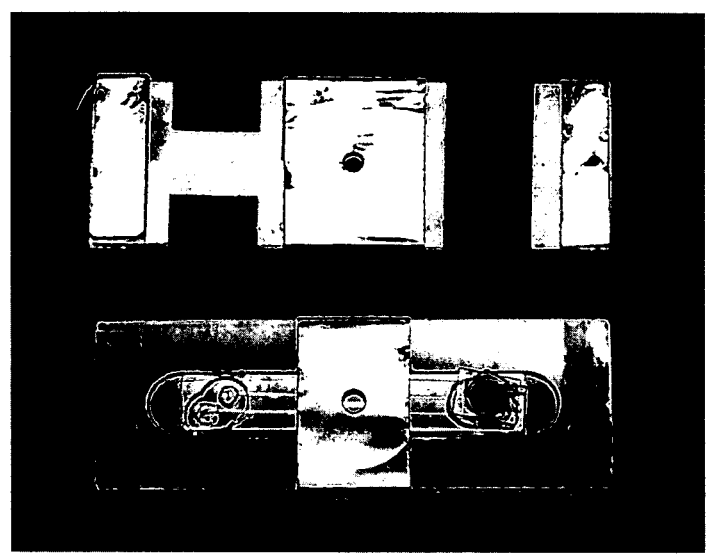
FIG. 12A is an illustration of a magnetic trap.
Figure 12B:
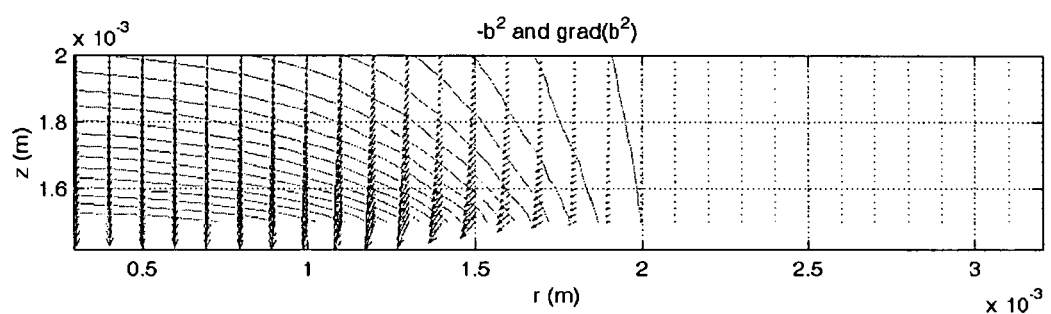
FIG. 12B shows the computed field distribution of quantities relevant to magneto-phoresis.

Trapping of magnetic beads was realized in a magnetic trap shown in FIG. 12A. This device comprises a bottom actuation element and a disposable top element that may host a channel system or a static reactor. In this example, it hosted an incubation chamber, as shown in FIG. 12A, which was formed by sandwiching 0.5 µl bead suspension droplet between a solid substrate and a 0.2-mm glass cover slip with 100-µm separation, and then by encapsulating the liquid phase with mineral oil. The magnetic actuator consists of a magnetic core, a coil, and high-permeability alloy layers that tune the field flux. In this particular embodiment, the device generates a magnetic field that is localized in a ⅛" circular region. To form an array of magnetic beads, a typical current below 100 mA was sufficient to generate a flux density gradient exceeding by more than two orders of magnitude that of an untuned coil without significantly increasing the flux density (<200 Gauss). Illustrated in FIG. 12B is the computed field distribution of quantities relevant to magneto-phoresis, namely, equipotential curves of $-b^2$, a quantity proportional to magneto-phoretic potential of an induced magnetic dipole moment, and vectors of its gradient, which is proportional to the relavent force. The induced magnetic field induces the magnetic beads in suspension to migrate towards a substrate. Once in proximity to the solid support, the beads interact with each other repulsively and reorganize into arrays in the reaction buffer. The beads are in a random state before the magnetic field is turned on.

Figure 13:
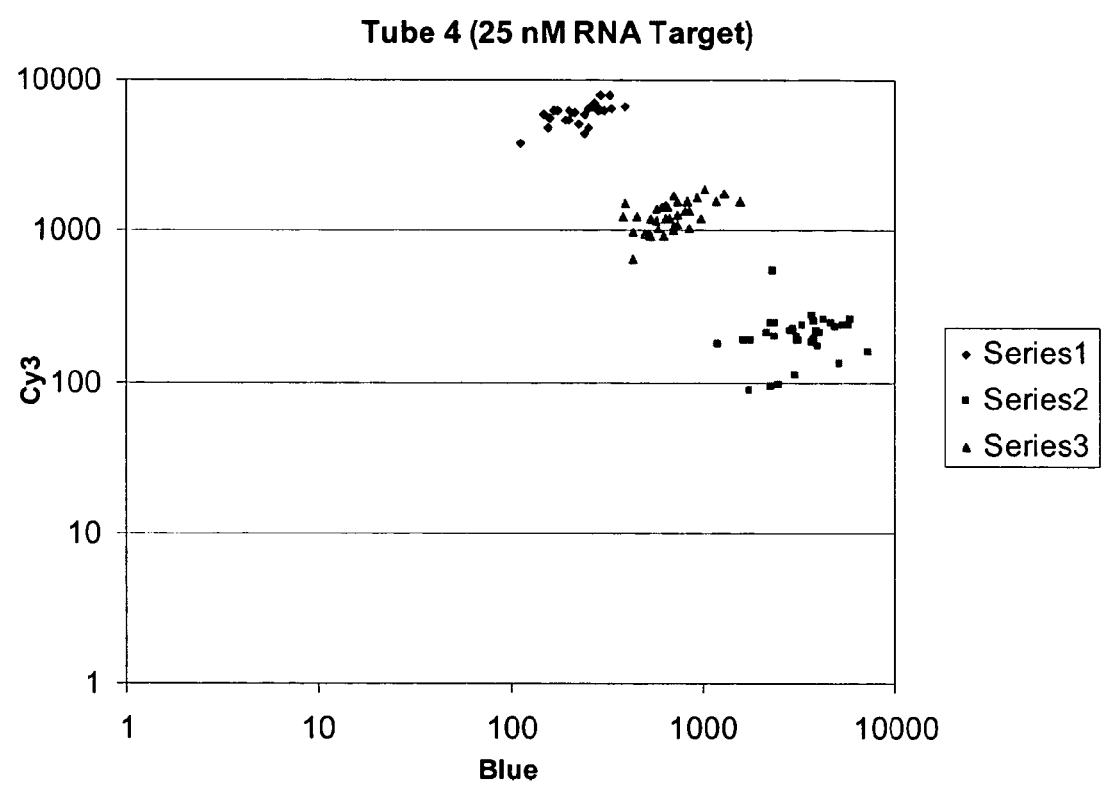
FIG. 13 shows bead-map plotted with Cy3 against blue, showing three clusters of beads.
Figure 14:
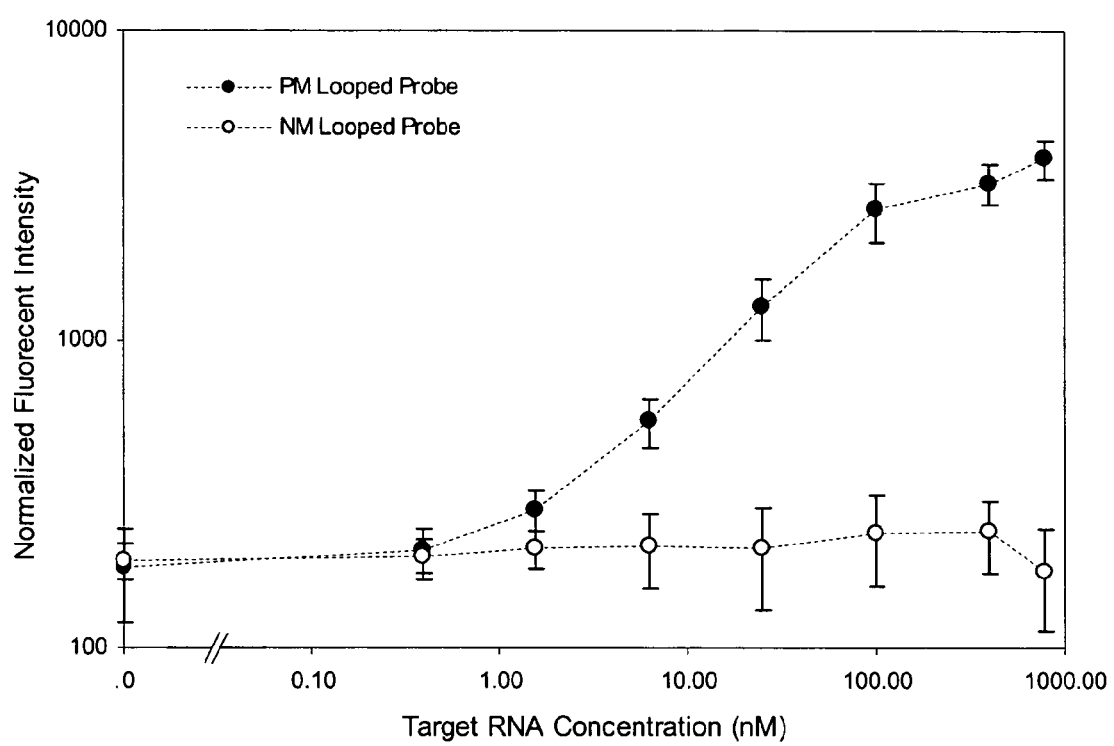
FIG. 14 shows the dose response of target interaction with specific and non-specific looped probes.

In this experiment, following incubation, bead suspension from each tube was transferred into the magnetic trap and, on activation, organized into arrays in accordance with the method described above. Optical interrogation was performed using fluorescence microscope (Nikon Eclipse E800). Image snapshots were taken through different optical filters, which are bright field, Cy3 filter (F5, 500 ms), green filter (F5, 200 ms), and blue field (F5, 150 ms), respectively. Images were processed using a Matlab code. Each single bead was identified and its corresponding Cy3 intensity was then registered to its blue intensity. In a "bead-map" (FIG. 13) plotted with Cy3 against blue, three clusters of beads can be seen and can be categorized to be B1, B2, B3, from left to right, respectively. The Cy3 intensity of B2 cluster indicates the magnitude of RNA-binding to the looped probes of specific type. After normalizing to the positive control (B1) for each sample. The dose response of target interaction with specific and non-specific looped probes are summarized in FIG. 14, with error bars representing standard deviation of the mean intensities.

It should be understood that the terms, expressions and examples herein are exemplary only and not limiting, and that the scope of the invention is defined only in the claims which follow, and includes all equivalents of the subject matter of the claims.

What is claimed is:

1. A method for array assembly and detection comprising:
   providing an incubation chamber;
   wherein the incubation chamber contains a suspension comprising nucleic acid targets, polymerase and a set of oligonucleotide probes bound to magnetic beads in a randomly dispersed state;
   wherein each probe comprises a target binding domain complementary to a target nucleic acid; a closing domain with a sequence that is complementary to the sequence of the target binding domain; and a joining region between the binding domain and the closing domain, which is not complementary to the target nucleic acid;
   placing the incubation chamber in a magnetic trap;
   generating a magnetic field, wherein the magnetic field induces the magnetic beads in suspension to migrate towards a substrate and, once in proximity to the substrate, the beads interact with each other repulsively and reorganize into arrays; and
   imaging the array.

2. The method of claim 1, wherein the magnetic trap comprises a bottom actuation element and a top element.

3. The method of claim 2, wherein the incubation chamber is placed in the top element.

4. The method of claim 2, wherein the magnetic trap further comprises a magnetic core, coil and high permeability layers.

5. The method of claim 1, wherein the nucleic acid targets are DNA or RNA.

6. The method of claim 1, wherein the oligonucleotide probes are DNA or RNA.

7. The method of claim 1, wherein the set of probes comprises at least two probes that differ in the sequence of their target binding domains.

8. The method of claim 1, wherein the probes are bound to a magnetic bead via the joining region.

9. The method of claim 1, further comprising placing the set of probes in contact with nucleic acid targets under conditions suitable for capture of the target by a probe and formation of a probe-target complex.

10. The method of claim 9, wherein the presence of probe-target complexes is detected in real time.

11. The method of claim 9, further comprising generating conditions suitable for enzyme-mediated probe elongation at the 3' terminal end if the nucleotide in the target sequence aligned with the 3' terminal end of the probe is complementary.

12. The method of claim 11, wherein labeled dNTPs or ddNTPs are incorporated into the elongated probe.

13. The method of claim 12, further comprising detecting probe-target-associated fluorescence by conducting a thermal stability analysis.

14. The method of claim 13, wherein the analysis is performed by cycling to a temperature above de-annealing temperature of non-elongated duplexes and then monitoring probe fluorescence to determine probe-target-associated fluorescence.

15. The method of claim 12, wherein the presence of probe-target complexes is detected in real time by monitoring probe fluorescence from the target-associated state of the probe and comparing it to the pre-assay signal.

16. The method of claim 11, wherein a reaction time is selected based on the stringency of the imposed conditions, the stringency determining the probability of random formation of a probe-target-enzyme-substrate intermediate state in the formation of elongation product, such that a sufficient number of stable elongated duplex states are capable of being formed.

17. The method of claim 1, wherein more than one type of oligonucleotide probe is bound to each magnetic bead.

18. The method of claim 1, wherein a bead map is generated indicating the location and amount of target bound to a probe.

* * * * *